(12) United States Patent
Boeck et al.

(10) Patent No.: US 8,733,341 B2
(45) Date of Patent: May 27, 2014

(54) ATOMIZER AND METHOD OF ATOMIZING FLUID WITH A NOZZLE RINSING MECHANISM

(75) Inventors: Georg Boeck, Laupheim (DE); Michael Spallek, Ingelheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1148 days.

(21) Appl. No.: 12/299,650

(22) PCT Filed: Apr. 16, 2007

(86) PCT No.: PCT/EP2007/003322
§ 371 (c)(1),
(2), (4) Date: Dec. 24, 2008

(87) PCT Pub. No.: WO2007/128381
PCT Pub. Date: Nov. 15, 2007

(65) Prior Publication Data
US 2009/0114215 A1 May 7, 2009

(30) Foreign Application Priority Data

May 10, 2006 (DE) .......................... 10 2006 022 002

(51) Int. Cl.
*A61M 15/00* (2006.01)
*A61M 15/02* (2006.01)
*A61M 11/00* (2006.01)

(52) U.S. Cl.
USPC ............ 128/200.14; 128/200.17; 128/200.21; 128/203.15; 128/203.23

(58) Field of Classification Search
USPC ............. 128/200.14–200.23, 203.15, 203.19, 128/203.21, 204.25; 222/148, 149, 153.11, 222/153.12, 319, 464.3; 604/68–72, 604/122–127

See application file for complete search history.

(56) References Cited

U.S. PATENT DOCUMENTS

| | | | | |
|---|---|---|---|---|
| 3,157,179 | A | * | 11/1964 | Allen et al. ............... 128/200.23 |
| 3,675,825 | A | * | 7/1972 | Morane .......................... 222/148 |
| 4,048,997 | A | * | 9/1977 | Raghavachari et al. ...... 604/189 |
| 5,433,343 | A | * | 7/1995 | Meshberg ........................ 222/25 |
| 5,497,944 | A | | 3/1996 | Weston |
| 5,593,069 | A | * | 1/1997 | Jinks ............................. 222/246 |
| 5,662,098 | A | * | 9/1997 | Yoshida ................... 128/200.22 |
| 5,662,271 | A | | 9/1997 | Weston |
| 5,833,088 | A | | 11/1998 | Kladders |
| 5,964,416 | A | | 10/1999 | Jaeger |
| 6,401,987 | B1 | | 6/2002 | Oechsel et al. |
| 6,402,055 | B1 | | 6/2002 | Jaeger et al. |

(Continued)

FOREIGN PATENT DOCUMENTS

| | | |
|---|---|---|
| CA | 2297174 A1 | 2/1999 |
| DE | 19733651 A1 | 2/1999 |

(Continued)

OTHER PUBLICATIONS

International Search Report for PCT/EP2007/003322 mailed Aug. 17, 2007.

*Primary Examiner* — Justine Yu
*Assistant Examiner* — Douglas Sul
(74) *Attorney, Agent, or Firm* — Michael P. Morris; Mary-Ellen M. Devlin (57) ABSTRACT

An atomizer and a method of dispensing and atomizing fluid into individual containers through a nozzle are proposed, where in order to improve the dosing accuracy, a preliminary amount of fluid, flushing the nozzle, is dispensed before each dose is dispensed.

16 Claims, 3 Drawing Sheets

(56) References Cited

U.S. PATENT DOCUMENTS

| | | |
|---|---|---|
| 6,578,741 B2 * | 6/2003 | Ritsche et al. ............ 222/153.13 |
| 6,890,517 B2 * | 5/2005 | Drechsel et al. ................ 424/45 |
| 2003/0145849 A1 * | 8/2003 | Drinan et al. ............ 128/200.14 |
| 2004/0015126 A1 * | 1/2004 | Zierenberg et al. ............. 604/72 |
| 2005/0061314 A1 * | 3/2005 | Davies et al. ............ 128/200.23 |
| 2005/0098172 A1 * | 5/2005 | Anderson ................ 128/200.23 |
| 2005/0183718 A1 | 8/2005 | Wuttke et al. |
| 2006/0285987 A1 | 12/2006 | Jaeger |
| 2008/0092885 A1 * | 4/2008 | von Schuckmann .... 128/203.15 |

FOREIGN PATENT DOCUMENTS

| | | |
|---|---|---|
| EP | 1003478 A1 | 5/2000 |
| JP | 2004097617 A * | 4/2004 |
| WO | 9114468 A1 | 10/1991 |
| WO | 9606011 A2 | 2/1996 |
| WO | 9712687 A1 | 4/1997 |
| WO | 98/12511 A2 | 3/1998 |

* cited by examiner

ATOMIZER AND METHOD OF ATOMIZING FLUID WITH A NOZZLE RINSING MECHANISM

This application is the national phase entry under 35 U.S.C. §371 of International Application No. PCT/EP2007/003322, filed Apr. 16, 2007, which claims priority to German Application No. DE 10 2006 022 002.1, filed May 10, 2006, each of which is hereby incorporated by reference in its entirety.

BACKGROUND

1. Field of the Invention

The present invention relates to an atomizer according to the preamble of claim 1, a process according to the preamble of claim 12 and a use of the atomizer.

2. Related Art

An atomizer is known under the brand name "Respimat" in the form of an inhaler as disclosed in general terms in WO 91/14468 A1 and specifically illustrated in WO 97/12687 A1 (FIG. 6a, 6b). The atomizer has, as a reservoir for a fluid which is to be atomised, an insertable container, a pressure generator with a drive spring and a nozzle through which the fluid is expelled and atomised.

After the container is used for the first time or left unused for any length of time, air in the pressure generator or nozzle system may cause the metering accuracy to be negatively affected when fluid is next expelled and atomised. This is not the case during the subsequent expulsion and atomisation, as any air present has been displaced by the fluid. Before the atomizer is used for the first time and after lengthy periods of non-use, it is therefore recommended that at least one dose of fluid should be expelled without being inhaled. This preliminary actuation is also referred to as "priming". Priming leads to an increased consumption of fluid and requires special care on the part of the user.

SUMMARY OF THE INVENTION

The aim of the present invention is to provide an atomizer and a process and a use of such an atomizer, such that particularly accurate metering is possible by simple means and with easy operation, and in particular so that there is no need for any priming.

This aim is achieved by an atomizer as disclosed and described herein.

A fundamental idea of the present invention is that in each case a preliminary amount of fluid, which is very small in relation to the dose, for rinsing the nozzle and any other delivery means of the atomizer in question, should be expelled preferably automatically before each intended delivery of a dose or each time the atomizer is tensioned. The term "intended" makes it clear that during the very first priming, the so-called dry priming, of the atomizer there is no intention of delivering a dose, nor is any dose delivered, and also no preliminary amount is expelled, in particular when initially only air is forced out of the conveying system of the atomizer. The delivery or production of the pre-spray has a number of advantages.

Rinsing with the preliminary amount can further improve the metering accuracy of the atomizer.

The air and other gases contained in the pressure generator or the like are displaced or at least substantially reduced by the preliminary amount. This improves the dosing accuracy during the next delivery.

The preliminary amount makes it possible for example to achieve a definite closure or other assumption of a defined position of a valve, particularly of the pressure generator, so that more defined states can be achieved during the actual use of the atomizer and dosing of the fluid intended for inhalation, in particular.

Moreover, thanks to the preliminary amount a defined break-off of fluid at the nozzle can be achieved, which corresponds substantially to that which occurs during the expulsion of fluid that takes place immediately after, as a result of which again the metering accuracy is further improved.

The rinsing of the nozzle by the preliminary amount can eliminate or detach deposits, contamination or microbial impurities.

Increases in concentration—e.g. as a result of evaporation during non-use—can also be reduced or prevented.

In the present invention, the term "rinsing the nozzle" preferably relates not only to the nozzle or nozzle system of the atomizer, but alternatively or additionally also relates to the pressure generator or other parts of the atomizer for conveying, expelling and atomising fluid, such as any filter, pressure chamber, valve, intake line, pressure line or the like which may be provided.

If oligodynamic silver compounds or other ion-releasing compounds are used in the atomizer, the silver ions or other ions may be expelled by the preliminary amount so that fewer ions are expelled and inhaled during actual use.

The proposed rinsing by the preliminary amount preferably occurs automatically, i.e. without separate operation or actuation by the user, particularly each time the atomizer or any spring contained therein is put under tension. Accordingly, very simple operation is achieved. Particularly preferably, the above-mentioned priming can be omitted altogether or at least reduced.

It has been found that a surprisingly small preliminary amount is sufficient in particular to achieve the advantages mentioned above. Even if the nozzle is rinsed with the preliminary amount on every actuation or use of the atomizer, the prospective overall fluid consumption is less, as priming leads to the expulsion of a full dose of fluid, even if it is not carried out before every use of the atomizer.

The preliminary amount of fluid is delivered as a spray mist and/or as drops, depending in particular on the pressure through the nozzle. The rinsing of the nozzle by the preliminary amount and its delivery through the nozzle—irrespective of whether it is in the form of a spray mist or drops—is also referred to as "pre-spray".

Further advantages, features, properties and aspects of the present invention will become apparent from the claims and the following description of a preferred embodiment by reference to the drawings.

BRIEF DESCRIPTION OF THE DRAWINGS

In the Figures the same reference numerals have been used for identical or similar parts, and corresponding or comparable properties and advantages are achieved even if the associated description is not repeated.

DETAILED DESCRIPTION OF THE INVENTION

Figure 1:
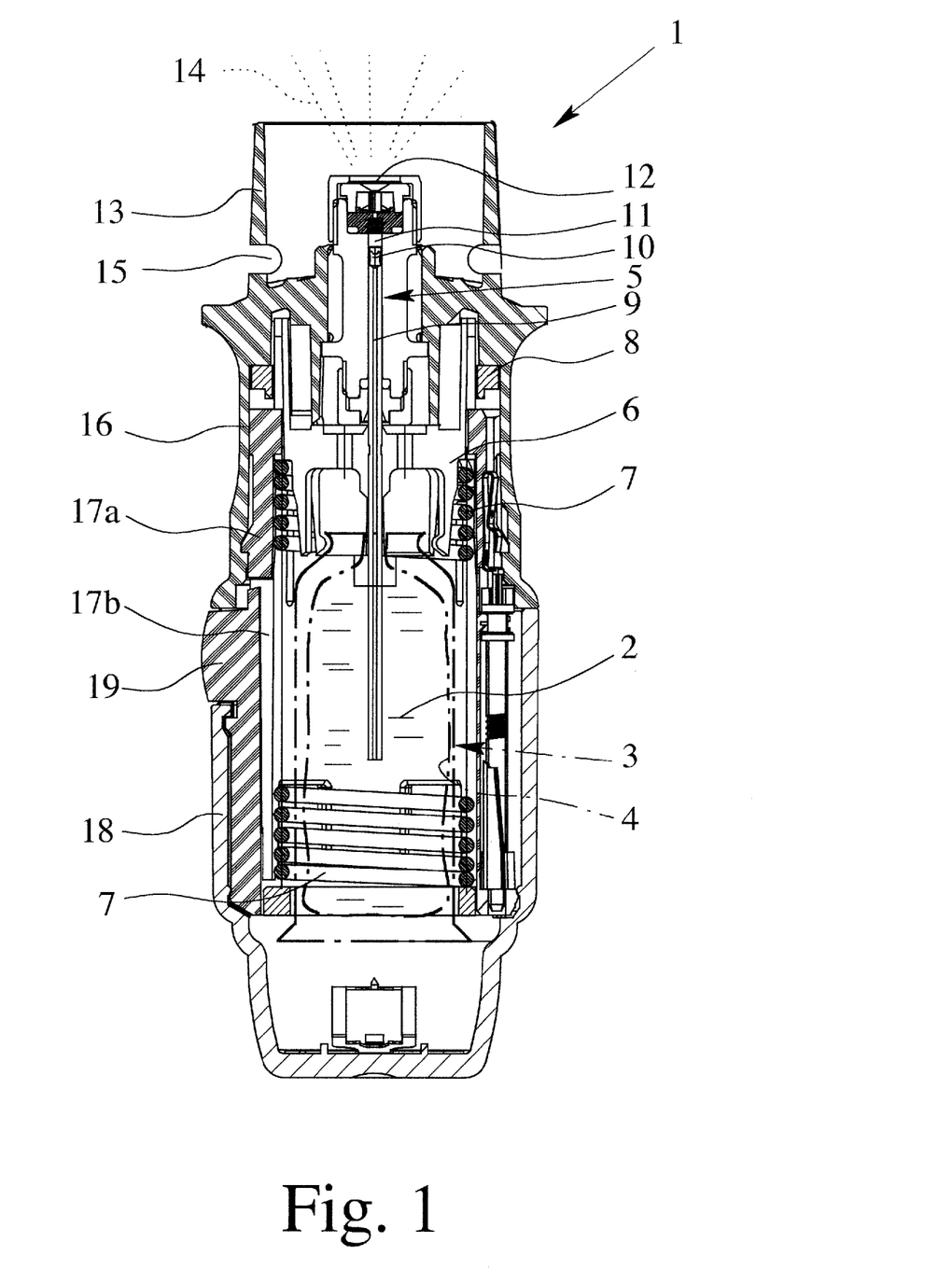
FIG. 1 is a schematic section through an atomizer in the non-tensioned state.
Figure 2:
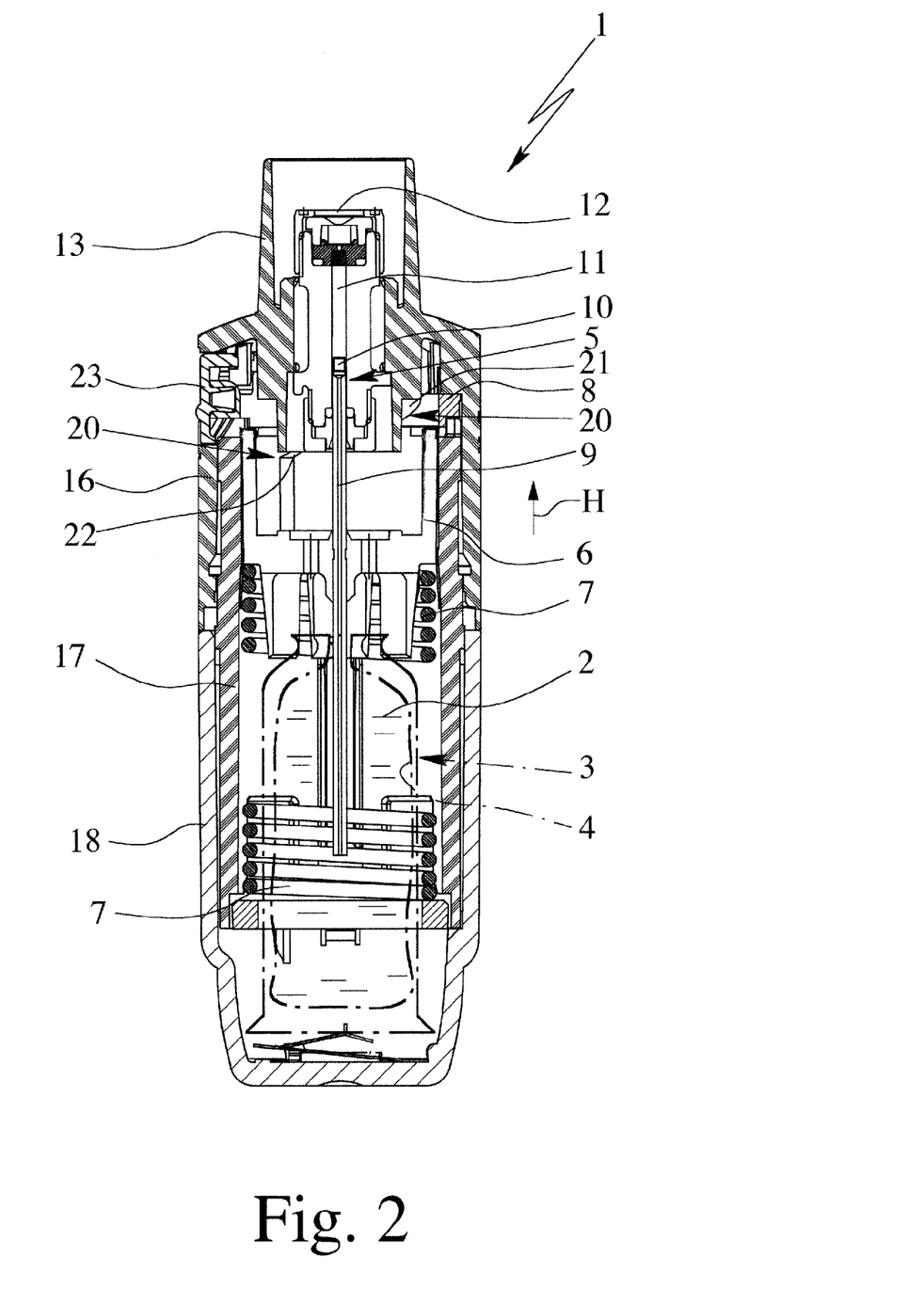
FIG. 2 is a schematic section through the atomizer in the tensioned state after rotation through 90° relative to FIG. 1.

FIGS. 1 and 2 show an atomizer 1 for atomising a fluid 2, particularly a highly effective medicament or the like, shown schematically in the non-tensioned state (FIG. 1) and in the tensioned state (FIG. 2). The atomizer 1 is embodied in particular as a portable inhaler and preferably operates without propellant gas.

Atomisation of the fluid 2, preferably a liquid, more particularly a medicament, produces an aerosol which can be breathed in or inhaled by a user (not shown). Normally, the medicament is inhaled at least once a day, more particularly several times a day, preferably at predetermined intervals, depending on the ailment affecting the patient.

The atomizer 1 has a preferably insertable and preferably replaceable container 3 containing the fluid 2. The container 3 thus forms a reservoir for the fluid 2 which is to be atomised, which is held in particular in a fluid chamber 4 formed by a collapsible bag in the container 3.

Preferably, the container 3 contains a sufficient amount of fluid 2 or active substance to provide, for example, up to 200 dosage units or doses, i.e. to allow up to 200 sprays or applications. A typical container 3 as disclosed in WO 96/06011 A2 holds a volume of about 2 to 10 ml.

The atomizer 1 also comprises a pressure generator 5 for delivering and atomising the fluid 2, particularly in a predetermined or adjustable dosage amount. The fluid 2 can thus be expelled and atomised in individual doses, particularly from about 5 to 30 µl.

The pressure generator 5 has a holder 6 for the container 3, an associated drive spring 7 which is only partly shown, a locking element 8 which is preferably manually operable to release it, a movable conveying element, particularly a conveying tube 9, a non-return valve 10, a pressure chamber 11 and a nozzle 12 in the region of a mouthpiece 13. The container 3 is fixed, particularly by latching, in the atomizer 1 via the holder 6 such that the conveying tube 9 dips into the container 3. The holder 6 may be embodied such that the container 3 can be detached and replaced.

For axially tensioning the drive spring 7, the holder 6 with the container 3 and the conveying tube 9 is moved downwards in the drawings and fluid 2 is sucked out of the container 3 through the non-return valve 10 into the pressure chamber 11 of the pressure generator 5.

During the subsequent release of tension after actuation of the locking element 8 to release the holder 6, the fluid 2 in the pressure chamber 11 is put under pressure by moving the conveying tube 9 with its now closed non-return valve 10 back upwards, by releasing the drive spring 7 (main movement), i.e. to act as a ram. This pressure expels the fluid 2 through the nozzle 12, during which time it is atomised into an aerosol 14, as indicated in FIG. 1.

A user or patient (not shown) can inhale the aerosol 14, while a supply of air can be sucked into the mouthpiece 13 through at least one air inlet opening 15.

The atomizer 1 has an upper housing part 16 and an inner part 17 which is rotatable relative thereto (FIG. 2) having an upper part 17a and a lower part 17b (FIG. 1), while an in particular manually operable housing part 18 is releasably attached to, in particular pushed onto, the inner part 17, preferably by means of a holding element 19. For inserting and/or changing the container 3, the housing part 18 can be detached from the atomizer 1.

The housing part 18 can be rotated relative to the upper housing part 16, carrying the inner part 17 with it. The upper part 17a rotates the holder 6 by corresponding engagement therewith, so that this holder is axially moved counter to the force of the drive spring 7 by means of a gear 20 which is merely indicated in FIG. 2 and the drive spring 7 is tensioned.

During tensioning, the container 3 is moved axially downwards. Finally, the container 3 assumes an end position as shown in FIG. 2. In this end position, the drive spring 7 is under tension. The locking element 8 can then secure the holder 6 and hence the conveying tube 9 and the container 3 against movement in the upward direction in the Figure, i.e. prevent the drive spring 7 from relaxing. In the view shown in FIG. 2 the holder 6 together with the conveying tube 9 and the container 3 and the drive spring 7 are in the tensioned state or in the tensioning position, but the locking element 8 is not in its transversely or radially shifted locking position that blocks the holder 6.

After the holder 6 has been released by the locking element 8—i.e. starting from the clamping position shown in FIG. 2 and in the position of the locking element 8 shown in FIG. 2—the atomising process takes place. The holder 6 together with the conveying tube 9 and the container 3 is returned to the starting position shown in FIG. 1 by the force of the drive spring 7. This movement is also referred to hereinafter as the main movement H, for short. During the main movement, the valve 10 is closed and the conveying tube 9 puts the fluid 2 contained in the pressure chamber 11 under pressure, so that this fluid is expelled through the nozzle 12 and atomised.

The container 3 thus preferably performs a lifting movement during the clamping process or for the withdrawal of fluid and during the atomising process.

In the embodiment shown the gear 20 for clamping the atomizer 1 or drive spring 7 and for axially moving the holder 6 in the tensioning direction preferably has sliding surfaces 21 and 22 on the upper housing part 18 and/or on the holder 6, which extend in particular in a helical configuration and lead to the desired axial movement of the holder 6 when the holder 6 is rotated relative to the upper housing part 16.

When the holder 6 reaches the clamping position shown in FIG. 2, the sliding surfaces 21, 22 move out of engagement, and the gear 20 releases the holder 6 for the opposite movement in the axial direction, particularly the main movement. At the same time, the locking element 8 is shifted into its locking position (shown in FIG. 3) transversely, particularly radially, to the axial movement or axial direction, such that the holder 6 and hence the conveying tube 9 and container 3 are blocked or secured in the tensioning position. In particular the locking element 8 is of annular construction and in its locking position is radially shifted out of the normally concentric arrangement with the holder 6, so that the holder 6 abuts with its end face on a portion of the locking element 8 and is blocked thereby.

To initiate the atomising process, the locking element 8 which is provided in particular with a button 23 or other actuating element is actuated and thereby moved back radially into its concentric position as shown in FIG. 2, as a result of which the blocking of the holder 6 is cancelled and the holder is able to perform the main movement in the direction of the arrow H. Any fluid 2 then contained in the pressure chamber 11 is expelled through the nozzle 12 and atomised.

The structure and mode of operation of a proposed atomizer are hereinafter explained by reference to the schematic sectional view in FIG. 3, which is not to scale and which substantially corresponds to the view in FIG. 2. The earlier remarks particularly relating to FIGS. 1 and 2 still apply or have a complementary value.

The proposed atomizer 1 is constructed so that before each delivery and atomisation of a dose of fluid 2 a specific preliminary amount of fluid 2 is expelled. This preliminary amount rinses the nozzle 12 or other conveying means, components or the like of the atomizer 1, particularly the conveying tube 9, the valve 10, the pressure chamber 11, a channel leading to the nozzle 12, an optional filter in front of the nozzle 12, the nozzle 12 or the like. The rinsing with the preliminary amount takes place in particular automatically on each actuation of the atomizer 1, particularly on each tensioning of the atomizer 1, and results in the pre-spray and the advantages described above.

The preliminary amount is preferably very small, but requires a certain minimum amount in order to achieve the desired advantages. It is preferably at least 0.5 μl, particularly 0.5 to 3 μl, most preferably about 1 to 2 μl. This is very little compared with the usual dose of fluid 2 (in particular about 15 to 20 μl), which is delivered on each atomisation. Preferably, the preliminary amount is at least 1%, more particularly at least 2%, most preferably about 3 to 10%, of the amount of a dose of the fluid 2 delivered during a normal atomisation process.

Particularly preferably, the preliminary amount is at least five times the volume of the nozzle 12 or of a nozzle block forming the nozzle 12. This of itself guarantees effective rinsing of the nozzle 12.

The following is an explanation of how the preliminary amount and the rinsing with the preliminary amount of fluid 2 are obtained.

Figure 3:
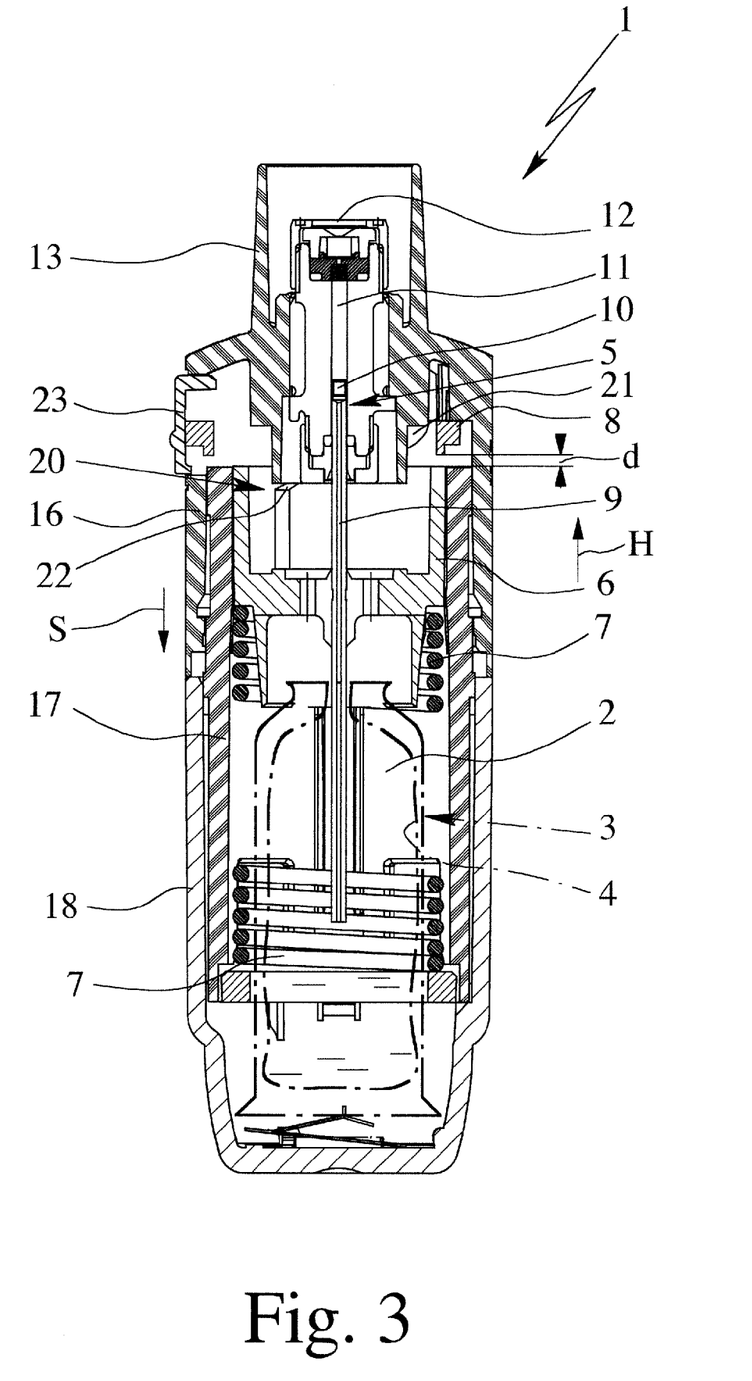
FIG. 3 is a schematic section through an atomizer with additional functionality.

During the tensioning of the atomizer 1 or the drive spring 7 in the tensioning direction S, the holder 6 and hence the conveying element 9 is moved into an over-tensioning position as shown in FIG. 3. In this over-tensioning position, the gear 20 releases the holder 6, so that an opposite movement can then take place as a result of the spring force, as in the normal atomisation process. The present invention envisages that a first movement—hereinafter referred to as the preliminary movement—takes place in this direction H, but initially only until the (normal) tensioning position is reached, i.e. until the holder 6 comes to abut on the locking element 8 which is in the locking position, in the embodiment shown. FIG. 3 shows the locking element 8 in the locking position with the button 23 extended. FIG. 2 shows the locking element 8 in the non-locking position, i.e. in the position in which the holder 6 is not blocked, with the button 23 pushed in, or in a concentric position.

The holder 6 and hence also the conveying element or conveying tube 9 automatically perform the preliminary movement into the tensioning position, from the over-tensioning position shown in FIG. 3, i.e. until blocked by the locking element 8. This preliminary movement, which preferably takes place in the same direction as the main movement H mentioned earlier during the normal atomising process, leads to the production and delivery of the desired preliminary amount of fluid 2.

The preliminary movement is very short by comparison with the main movement. In particular its stroke d, i.e. the distance from the over-tensioning position into the tensioning position, is only about 0.2 to 1 mm, in particular about 0.4 to 0.8 mm.

If required, the stroke d may be adjusted or fixed to adapt to the nozzle 12, the pressure generator 5 or the like and/or to adapt to the particular fluid 2. The volume of the preliminary amount can be varied accordingly by varying the stroke d.

Depending on the volume of the preliminary amount and the pressure increase—particularly the speed of return of the conveying element or conveying tube 9 from the over-tensioning position into the clamping position—and depending on the fluid 2, the preliminary amount is expelled in the form of drops and/or as a spray mist or spray jet. The user can if necessary wipe or shake off the drop and optionally other residual amounts of fluid 2 remaining on the nozzle 12 during normal use of the atomizer 1. Alternatively or additionally, the drop or the residual amounts can also be wiped away or absorbed by means of a covering cap (not shown) for closing off the mouthpiece 13, particularly a wiper or absorption means, such as a piece of non-woven fabric or the like, accommodated in the covering cap.

The covering cap may be of transparent construction, at least in parts, so that the user can monitor the expulsion of the preliminary amount. Alternatively, it is also possible that the user will not monitor the expulsion of the preliminary amount and in particular will not notice it either. In fact, the expulsion of the preliminary amount may take place almost imperceptibly and so fast that it does not interfere with the normal handling and use of the atomizer 1 for delivering and atomising fluid 2.

According to a further feature (not shown) an additional barrier or delay may be provided, so that the tensioned atomizer 1—i.e. the tensioning element 8 or the button 23 in this embodiment—can only be actuated when the preliminary amount of fluid 2 has been expelled or the holder 6 and the conveying tube 9 have reached the tensioning position, i.e. the holder 6 is abutting on the locking element 8. This is a way of preventing the preliminary amount from being expelled and atomised together with the actual dose of fluid 2, i.e. so that the normal dose is undesirably increased by the preliminary amount.

After the preliminary amount has been expelled, the user can operate the atomizer 1 completely normally, in particular by pressing the button 23 to move the locking element 8 out of the locking position into the position, which is concentric in this embodiment, which does not block the holder 6. Thus the holder 6 is freed and normal delivery and atomisation take place. As a result of the spring force of the drive spring 7 the conveying tube 9 performs the main movement H, while any fluid 2 contained in the pressure chamber 11 is expelled and atomised through the nozzle 12.

Surprisingly, it was found that the deliberately selected preliminary amount can be used to rinse the nozzle 12 or the entire nozzle or delivery system, in particular in order to expel or detach any deposits, dirt or microbial contamination immediately before using the atomizer 1, i.e. immediately before inhalation, in particular. The proposed rinsing with the preliminary amount also decreases the risk of blockage of the nozzles caused by deposits, contamination, crystallisation or the like.

In addition, undesirable increases in concentration, particularly in the nozzle region, can be avoided or at least minimised. Such concentrations—e.g. an undesirable increase in an active substance or other material—occur particularly with fluids 2 that contain solvent, particularly ethanolic or ethanol-containing fluids 2. The prevention or reduction of concentrations in the nozzle region also helps to ensure greater metering accuracy.

The metering accuracy can also be further improved by the fact that the preliminary amount moistens parts of the pressure generator 5 or nozzle system before they are actually used.

A particular advantage of the proposed rinsing with the preliminary amount is that it occurs on each actuation, particularly each tensioning, of the atomizer 1—i.e. in particular automatically—and cannot or need not be influenced by the user.

The proposed rinsing can also be used to improve the microbiological condition of the inhaler still further. In particular, any pathogens formed are expelled. If oligodynamic silver compounds are used in the atomizer 1, any silver ions produced are expelled by the rinsing with the preliminary amount, so that fewer silver ions are delivered and inhaled.

The proposed rinsing with the preliminary amount also causes the valve 10 to be moved into a defined closed position, so that during the subsequent actual operation of the atomizer 1, the fluid 2 is immediately put under pressure and expelled. The closure time of the valve 10 is in fact reduced and stabilised. As a result the variability of the volume delivered is reduced, i.e. a further improvement in the metering accuracy can be obtained.

The above-mentioned effects and advantages can be obtained with a surprisingly small preliminary amount, in particular with the volumes or ratios mentioned hereinbefore.

It should be noted that the proposed rinsing before the actual delivery of the fluid can generally be implemented in other atomizers as well. In particular other constructional solutions and alternatives to the proposed rinsing or production of the preliminary amount can also be used. Different constructional solutions to the locking and unlocking in the tensioning position are also possible. Generally, instead of the drive spring 7 it is also possible to use a different spring or drive means. Even if the conveying element is manually driven in the main direction or direction of delivery, it is possible to produce and expel the preliminary amount for rinsing purposes.

In contrast to freestanding apparatus or the like, the proposed atomizer 1 is preferably designed to be portable and in particular it is a mobile hand-held device.

However, the proposed solution may be used not only in the atomizers 1 that are specifically described here but also in other atomizers or inhalers, e.g. powder inhalers or so-called "metered dose inhalers".

The atomizer 1 is particularly preferably embodied as an inhaler, particularly for medicinal aerosol therapy. Alternatively, however, the atomizer 1 can also be designed for other uses, preferably for atomising a cosmetic liquid and particularly as a perfume atomizer. The container 3 correspondingly contains, for example, a medicament formulation or a cosmetic liquid such as perfume or the like.

Preferably, the fluid 2 is a liquid as already mentioned, in particular an aqueous or ethanolic medicament formulation. However, it may also be some other medicament formulation, a suspension or the like or particles or powder.

Some preferred ingredients and/or formulations of the preferably medicinal fluid 2 are listed below. As already mentioned, they may be aqueous or non-aqueous solutions, mixtures, ethanol-containing or solvent-free formulations. Particularly preferably, the fluid 2 contains:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide

4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

AC-1-en wherein X⁻ may have the above-mentioned meanings. Other preferred anticholinergics are selected from the salts of formula AC-2

AC-2 wherein R denotes either methyl or ethyl and wherein X⁻ may have the above-mentioned meanings. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;

tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the pre-sent invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3 S-yl)6,9-difluoro-1,1-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydro furan-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy]-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydro furan-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules as disclosed in EP 1 003 478 A1 or CA 2297174 A1.

In addition, the compound may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

LIST OF REFERENCE NUMERALS 1 atomizer
2 fluid
3 container
4 fluid chamber
5 pressure generator
6 holder
7 drive spring
8 locking element
9 conveying tube
10 non-return valve
11 pressure chamber
12 nozzle
13 mouthpiece
14 aerosol
15 air inlet opening
16 upper housing part
17 inner part
17a upper part of the inner part
17b lower part of the inner part
18 housing part (lower part)
19 holding element
20 gear
21 sliding surface
22 sliding surface
23 button
H main movement
S tensioning movement
d stroke

The invention claimed is:

1. An atomizer (1) for a fluid (2), comprising:
a fluid reservoir in the form of a container (3);
a nozzle (12) for the delivery and atomization of the fluid (2), wherein the fluid (2) is delivered in metered individual full-doses; and
a conveying element in the form of a conveying tube (9), which is movable for conveying the fluid, which is movable: (i) in a preliminary movement to a tensioning position for delivering a preliminary amount of the fluid, and thereafter (ii) in a main movement for delivering a full-dose for actual delivery and atomization of the fluid (2), wherein the conveying element is movable counter to a spring force by at least one of: (i) a gear (20), and (ii) manual actuation of the atomizer (1) into an over-tensioning position from which the conveying element is moved by spring force into the tensioning position,
wherein the preliminary amount of fluid (2), which is substantially less than a metered individual full-dose, rinses the nozzle (12) and is delivered before delivery of each metered individual full-dose or on each tensioning of the atomizer (1).

2. The atomizer according to claim 1, wherein the preliminary amount is between 0.5 to 3.0 microliters.

3. The atomizer according to claim 1, wherein the preliminary amount is one of: (i) between 1 to 10 percent of an amount of each full-dose and (ii) at least five times a volume of the nozzle (12).

4. The atomizer according to claim 1, wherein the preliminary movement and main movement are carried out exclusively by spring force.

5. The atomizer according to claim 1, wherein a stroke (d) of the preliminary movement is 0.2 to 1 millimeters.

6. The atomizer according to claim 1, wherein the atomizer (1) has a locking element (8) which in a locking position secures the conveying element directly or indirectly in the tensioning position and can be moved manually out of the locking position in order to release the conveying element.

7. The atomizer according to claim 1, wherein the atomizer (1) contains a fluid (2) that contains a solvent.

8. The atomizer according to claim 1, wherein the atomizer (1) contains an inhalable formulation or a medicament in the form of a fluid (2), selected from anticholinergics, betamimetics, steroids, phosphodiesterase IV-inhibitors, LTD4-antagonists and EGFR-kinase-inhibitors, antiallergics, ergot alkaloid derivatives, triptans, CGRP-antagonists, phosphodiesterase-V-inhibitors, and any combination of each of the foregoing.

9. The atomizer according to claim 1, wherein the atomizer (1) is constructed as a portable inhaler for medicinal aerosol therapy.

10. The atomizer according to claim 1, wherein the fluid includes a medicament selected from anticholinergics, betamimetics, steroids, phosphodiesterase IV-inhibitors, LTD4-antagonists and EGFR-kinase-inhibitors, antiallergics, ergot alkaloid derivatives, triptans, CGRP-antagonists, phosphodiesterase-V-inhibitors, and any combination of each of the foregoing.

11. A method for delivering and atomizing fluid (2), which is delivered in individual, metered full-doses through a nozzle (12), the method comprising:
moving a conveying element in the form of a conveying tube (9) for conveying the fluid in a preliminary movement to a tensioning position for delivering a preliminary amount of the fluid; and
thereafter moving the conveying element in a main movement for delivering an individual metered full-dose for actual delivery and atomization of the fluid (2), wherein the conveying element is movable counter to a spring force into an over-tensioning position, and from which the conveying element is moved by spring force into the tensioning position, and
wherein the preliminary amount of fluid (2) is substantially less than the individual metered full-dose, and rinses the nozzle (12) before delivery of each individual metered full-dose or on each tensioning of the atomizer (1).

12. The method according to claim 11, wherein the preliminary amount is between 0.5 and 3.0 microliters.

13. The method according to claim 11, wherein the preliminary amount is between 1 to 10 percent of the amount of the full-dose.

14. The method according to claim 11, wherein the preliminary movement and main movement are carried out exclusively by spring force.

15. The method according to claim 11, wherein a stroke (d) of the preliminary movement is 0.2 to 1 millimeters.

16. The method according to claim 11, wherein the conveying element is released in the tensioning position by manual operation of a locking element (8).

* * * * *

UNITED STATES PATENT AND TRADEMARK OFFICE
CERTIFICATE OF CORRECTION

| | | |
|---|---|---|
| PATENT NO. | : 8,733,341 B2 | Page 1 of 1 |
| APPLICATION NO. | : 12/299650 | |
| DATED | : May 27, 2014 | |
| INVENTOR(S) | : Boeck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1279 days.

Signed and Sealed this
Twenty-fifth Day of August, 2015

Michelle K. Lee
*Director of the United States Patent and Trademark Office*